(12) United States Patent
Carter

(10) Patent No.: US 6,949,691 B2
(45) Date of Patent: Sep. 27, 2005

(54) HUMAN ALBUMIN ANIMAL MODELS FOR DRUG EVALUATION, TOXICOLOGY AND IMMUNOGENICITY STUDIES

(75) Inventor: Daniel C. Carter, Huntsville, AL (US)

(73) Assignee: New Century Pharmaceuticals Inc., Huntsville, AL (US)

( * ) Notice: Subject to any disclaimer, the term of this patent is extended or adjusted under 35 U.S.C. 154(b) by 0 days.

(21) Appl. No.: 10/171,688

(22) Filed: Jun. 17, 2002

(65) Prior Publication Data

US 2003/0033615 A1 Feb. 13, 2003

Related U.S. Application Data

(60) Provisional application No. 60/298,124, filed on Jun. 15, 2001.

(51) Int. Cl.$^7$ .................... A01K 67/027; G01N 33/00
(52) U.S. Cl. ............................. 800/18; 800/3
(58) Field of Search ............... 800/18, 3, 14; 424/9.2

(56) References Cited

U.S. PATENT DOCUMENTS

| | | | |
|---|---|---|---|
| 4,736,866 A | | 4/1988 | Leder et al. |
| 4,873,191 A | | 10/1989 | Wagner et al. |
| 5,416,017 A | | 5/1995 | Burton et al. |
| 5,631,407 A | | 5/1997 | Racaniello et al. |
| 5,633,076 A | * | 5/1997 | DeBoer et al. ............... 800/25 |
| 5,741,957 A | | 4/1998 | Deboer et al. |
| 5,767,337 A | | 6/1998 | Roses et al. |
| 5,780,594 A | | 7/1998 | Carter |
| 5,948,609 A | | 9/1999 | Carter et al. |
| 6,194,633 B1 | | 2/2001 | Koretzky et al. |
| 6,291,243 B1 | | 9/2001 | Fogarty et al. |

FOREIGN PATENT DOCUMENTS

WO    WO 96/04376    2/1996

OTHER PUBLICATIONS

McCreath, 2000, Nature, vol. 405, pp. 1066–1069.*
Denning, Jun. 2001, Nature Biotechnology, vol. 19, pp. 559–562.*
Dinnyes, 2002, Cloning and Stem Cells, vol. 4, pp. 81–90.*
Polejaeva, I.A. 2001, Control of Pig Reproduction VI, Reproduction, Suppl. vol. 58, pp. 293–300.*
Cameron, 1997, Molec. Biotech. vol. 7, pp. 253–265.*
Niemann, 1997, Transg. Res. vol. 7, pp. 73–75.*
Campbell and Wilmut, 1997, Theriogenology, vol. 47, pp. 63–72.*
Dorland's Medical Dictionary, "animal model", http://www.mercksource.com/pp/us/cns/cns_hl_dorlands.jspzQzpg-zEzzSzppdocszSzuszSzcom-monzSzdorlandszSzdorlandzSzdmd_m_17zPzhtm#1046148.*
Overbeek, 1994, "Factors affecting transgenic animal production," Transgenic animal technology, pp. 96–98.*
Wall, 1996, Theriogenology, vol. 45, pp. 57–68.☐☐.*
Houdebine, 1994, J. Biotech. vol. 34, pp. 269–287.*
Kappell, 1992, Current Opionions in Biotechnology, vol. 3, pp. 548–553.☐☐.*
Milici et al., "Transcytosis of Albumin in Capillary Endothelium", The Journal of Cell Biology, vol. 105 (No. 6, Pt. 1), Dec. 1987, pp. 2603–2612.
Schnitzer et al., "Albumin interacts specifically with a 60–kDa microvascular endothelial glycoprotein", Proc. Natl. Acad. Sci., vol. 85, Sep. 1988, pp. 6773–6777.
Nomura, "Practical Development of Genetically Engineered Animals as Human Disease Models", Laboratory Animal Science, vol. 47, No. 2, Apr. 1997, pp. 113–117.

* cited by examiner

Primary Examiner—Joseph Woitach
Assistant Examiner—Valarie Bertoglio
(74) Attorney, Agent, or Firm—Stitues & Harbison PLLC; B. Aaron Schulman

(57) ABSTRACT

An animal model is provided which is genetically engineered to express human serum albumin, and such animals may be advantageously used in assessing drugs, vaccines or other therapeutic compounds that may be used in humans. In addition, an animal model is provided which does not manufacture its own albumin and which has been injected with human serum albumin. Through the use of these animal models, drugs and other chemicals can be more accurately assessed in physiological environments that reflect the conditions to be expected in humans, and such models will be useful in assessing new drugs and evaluating toxic substances for potential dangers as carcinogens, mutagens, etc. Other applications include evaluating immunological properties of various albumin-engineered proteins which might be administered to humans as therapeutics or vaccines, and research of disease states, such as genetic diseases, to provide further insight in treating these diseases.

5 Claims, 1 Drawing Sheet

Figure 1:
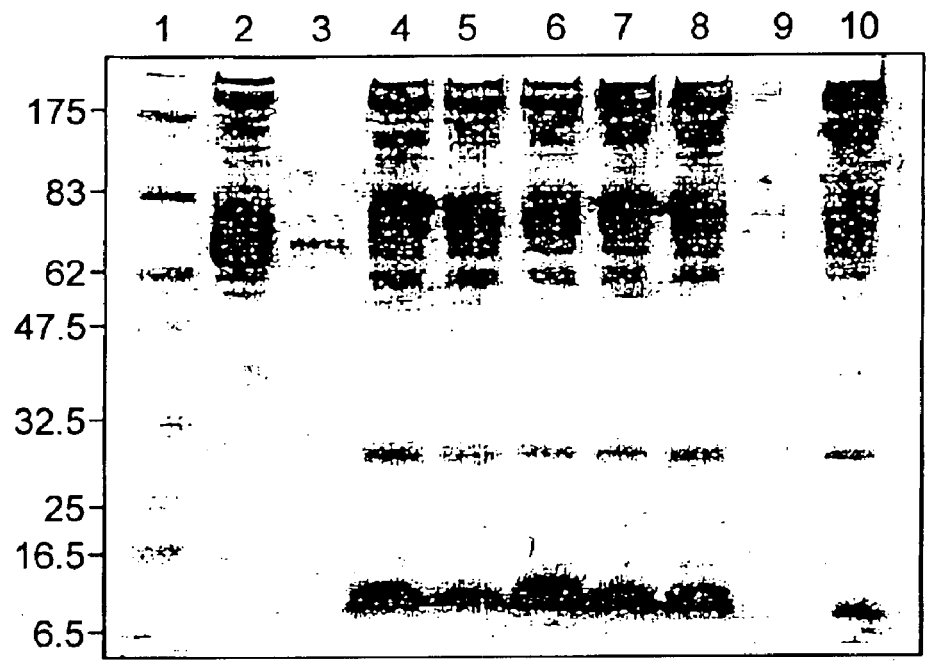

HUMAN ALBUMIN ANIMAL MODELS FOR DRUG EVALUATION, TOXICOLOGY AND IMMUNOGENICITY STUDIES

CROSS-REFERENCE TO RELATED APPLICATIONS

This application claims the benefit of U.S. Provisional Application Ser. No. 60/298,124, filed Jun. 15, 2001.

FIELD OF THE INVENTION

This invention relates in general to an animal model with serum attributes which have similar or identical properties and pharmokinetics with the human blood system in order to improve the assessment and development of new therapeutics and vaccines and to provide more reliable systems for identifying chemicals or drugs that may be carcinogenic or toxigenic to humans, and more specifically relates to transgenic animals and other animal models which contain and/or express human serum albumin and which thus can be used in methods of drug evaluation, toxicology and immunogenicity so as to provide a far more accurate picture of how drugs and chemicals will react in humans than would be possible through the conventional testing of animals that do not express human serum albumin.

BACKGROUND OF THE INVENTION

The serum albumins belong to a multigene family of proteins that includes alpha-fetoprotein and human group-specific component, also known as vitamin-D binding protein. The members of this multigene family are typically comprised of relatively large multi-domain proteins, and the serum albumins are the major soluble proteins of the circulatory system and contribute to many vital physiological processes. Serum albumin generally comprises about 50% of the total blood component by dry weight, and as such is responsible for roughly 80% of the maintenance of colloid osmotic blood pressure and is chiefly responsible for controlling the physiological pH of blood.

The albumins and their related blood proteins also play an extremely important role in the transport, distribution and metabolism of many endogenous and exogenous ligands in the human body, including a variety of chemically diverse molecules including fatty acids, amino acids, steroids, calcium, metals such as copper and zinc, and various pharmaceutical agents. The albumin family of molecules are generally thought to facilitate transfer of many of these ligands across organ-circulatory interfaces such as the liver, intestines, kidneys and the brain, and studies have suggested the existence of an albumin cell surface receptor. See, e.g., Schnitzer et al., P.N.A.S. 85:6773 (1988). The albumins are thus involved in a wide range of circulatory and metabolic functions.

Human serum albumin (HSA) is a protein of about 66,500 kD and is comprised of 585 amino acids including at least 17 disulphide bridges. As with many of the members of the albumin family, human serum albumin plays an extremely important role in human physiology and is located in virtually every human tissue and bodily secretion. Human serum albumin is the major protein of the circulatory system and as such is involved in the attachment, distribution and metabolism of all known pharmaceuticals because of its particular binding affinities to these chemicals. The atomic structure and particular details regarding the binding affinities of albumin and the specific regions primarily responsible for those binding properties have been previously determined as set forth, e.g., in U.S. Ser. No. 08/448,196, filed May 25, 1993, now U.S. Pat. No. 5,780,594 and U.S. Ser. No. 08/984,176, filed Dec. 3, 1997, now U.S. Pat. No. 5,948,609, both of which are incorporated herein by reference. Other articles or references of relevance with regard to human serum albumin include Carter et al., *Advances in Protein Chemistry*, 45:153–203 (1994); Peters, Jr., "All About Albumin", Academic Press (1995); Camerman et al., *Can J. Chem.*, 54:1309–1316 (1976); Lau et al., *J. Biol. Chem.*, 249:5878–5884 (1974); Callan et al., *Res. Commun. Chem. Pathol. Pharmacol.*, 5:459–472 (1973); and Nieboer et al., *Br. J. Ind. Med.*, 41:56–63 (1984); and all of these references are incorporated by reference as well.

It is also widely known and understood that the amino acid sequences in the different animals vary from humans in differing degrees, from essentially 98% homology for chimpanzees to a more typical value of approximately 60% for other animals such as dogs, mice, rats, etc. While data has shown the overall conservation of the three-dimensional structure of albumin from other species, the specific residues involved in the ligand binding chemistry are distinctly different and account for sometimes quite different pharmokinetics and toxicity involving drug experiments with animal models. As a result, the literature is replete with examples of drugs which appeared to be extremely effective in animal testing only to show extremely disappointing results when used in human trials.

There is thus a significant need to develop new animal models which can more accurately be utilized in toxicological and pharmokinetic studies so as to more accurately reflect how a particular drug or other chemical will work in humans.

SUMMARY OF THE INVENTION

Accordingly, it is thus an object of the present invention to create animal models which supplement or replace the natural albumin sequence with a typical human serum albumin sequence and which thus will be far more effective in providing an accurate assessment of how drugs or other chemicals will react in humans.

It is another object of the present invention to create transgenic animals which contain and/or express human serum albumin and which will thus be far more useful in methods of drug evaluation, toxicology and immunogenicity and provide a far more accurate picture of how drugs, chemicals and vaccines will react in humans than would be possible through conventional testing of animals that do not express human albumin.

It is still further an object of the present invention to create a variety of transgenic animals from a variety of species which will contain and express human serum albumin and which will thus be far more useful in assessing the safety and efficacy of new drugs, vaccines, or other medicaments.

It is yet another object of the present invention to provide even further animal models for assessing the safety and efficacy of materials such as drugs or vaccines which are intended to be administered internally to humans, said models which are either natural mutants which do not express their own serum albumin or mammals which have had the gene for serum albumin knocked out, and such models can be injected with human serum albumin which is retained in these mammals and thus provides an animal model for assessing drugs or vaccines in humans more accurately than in animal models which do not contain or express human serum albumin.

It is still further an object to provide hybrid non-human mammals which are transfected with the gene for human serum albumin yet maintain their own expression of serum albumin, and thus such hybrid animals may be used in methods of testing or assessing internal medicines, or in research involving administration of such medicines in cases with a given percentage of human serum albumin versus a given percentage of a serum albumin from a non-human mammal.

It is even further an object of the present invention to provide a method for assessing human drugs or vaccines, or other chemicals which may be utilized in compositions taken by or applied to humans, by which the drug, vaccine or chemical can be assessed in a manner more likely to be consistent with the way that these materials will be handled by the human body.

It is yet a further object of the present invention to provide animal models which reflect the various genetic diseases and disease states and which also incorporate and express a gene for human serum albumin so as to be useful in methods of assessing drugs utilized to treat or prevent genetic diseases or disease conditions caused by other pathogens.

These and other objects are achieved by virtue of the present invention which provides animal models wherein the animal contains human serum albumin in its bloodstream, either through genetic engineering to transfect a gene coding for human serum albumin, either in conjunction with or as an alternate to the animal's own genes for producing albumin, or through the use of animals which do not produce their own native albumin and which have been injected with human serum albumin which is retained in their bloodstream. The invention also provides methods of preparing such animals and of using such animals in the assessment of drugs, vaccines, chemicals or any other materials that may be used on humans. Having distributions of the drugs in the circulatory system which directly reflect the conditions to be expected in humans is of tremendous value to the pharmaceutical industry and also has great application in the evaluation of various toxic substances for potential dangers as carcinogens, mutagens, etc. In addition, there are numerous applications involving the evaluations of immunogenicity or other immunological properties of various albumin-engineered proteins which might be administered to humans as therapeutics or vaccines, and these will also now be able to be assessed in animal models for closely following the human blood system.

The animal models of the present invention, including transgenic animals expressing human serum albumin as well as other models such as mutant rats which do not produce their own albumin and which can be injected with human serum albumin, can thus be used advantageously so as to assess drugs or other internal medicines for their effect in the human bloodstream and/or their reactions to a more normal human setting, namely a bloodstream having human serum albumin therein. In addition, it is also possible to employ the transgenic animals in accordance with the present invention for the large-scale production of human serum albumin when such production is desired.

These and other features of the present invention as set forth in, or will become obvious from, the detailed description of the preferred embodiments provided hereinbelow.

BRIEF DESCRIPTION OF THE DRAWING FIGURES

FIG. 1 is a chromatograph showing the results of human serum albumin testing involving animal model ODNAR10 in accordance with the invention, including lane 1, the molecular weight marker, lane 2, a Sprague-Dawley (SD) control rat, lane 3, blank, lane 4, NAR control rat, lane 5, serum from female NAR rat 22, lane 6, serum from female NAR rat 23, lane 7, serum from female NAR rat 24, lane 8, serum from male NAR rat 30, lane 9, blank, and lane 10, blood sample from ODNAR10 after fifth bleed.

Figure 2:
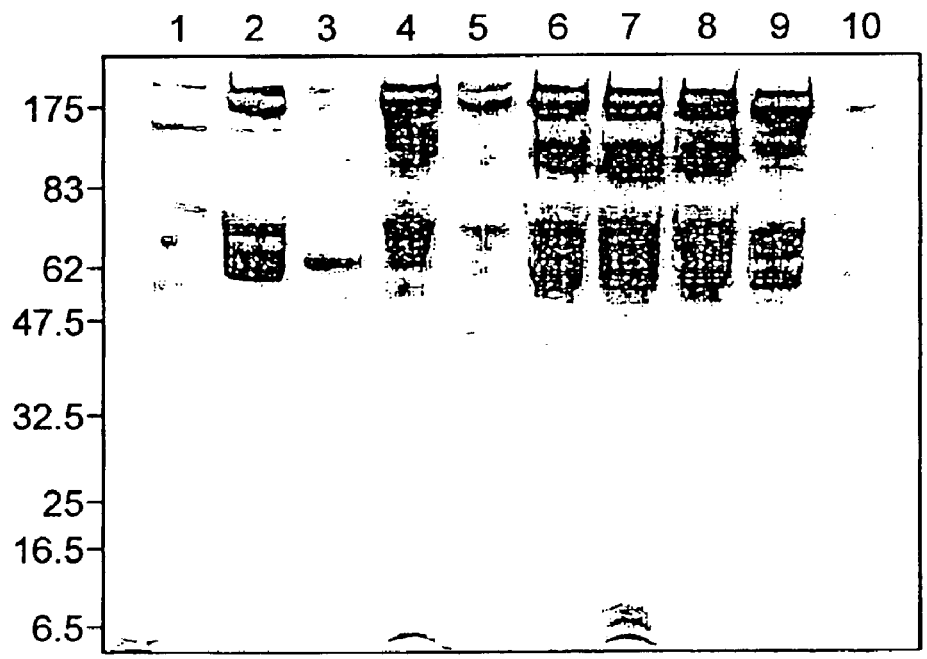

FIG. 2 is a chromatograph showing the results of human serum albumin testing involving animal model ODNAR14 in accordance with the invention, including lane 1, the molecular weight marker (New England Biolabs, Prestained Protein Marker, Broad Range #P7708S, premixed, Lot 25), lane 2, SD control rat, lane 3, blank, lane 4, pre-HSA injection bleed of ODNAR14, lane 5, blank, lane 6, ODNAR14 after $4^{th}$ post-injection bleed, lane 7, ODNAR14 after $3^{rd}$ post-injection bleed, lane 8, ODNAR14 after $2^{nd}$ post-injection bleed, lane 9, ODNAR14 after $1^{st}$ post-injection bleed, lane 10, blank.

DETAILED DESCRIPTION OF THE PREFERRED EMBODIMENTS

In accordance with the present invention, animal models are provided which contain and/or express human serum albumin either in conjunction with, or as an alternative to, the animal's own genes for producing albumin. The amino acid and nucleic acid sequences for human serum albumin are known and have been disclosed, e.g., in U.S. Pat. No. 5,780,594 (Carter et al.) and in the journal articles Hawkins et al., Gene 19(1):55–8 (1982) and Lawn et al., Nucleic Acids Res. 9(22):6103–114 (1981), all herein incorporated by reference. In one preferred mode of the invention, the transgenic animal models of the present invention are constructed via genetic engineering of an appropriate animal so that genes coding for human serum albumin are incorporated into the genome of the animal which is then able to express human serum albumin. In one embodiment, this genetically engineered animal may be constructed through the introduction of genes coding for human serum albumin without knocking out the animal's own genes for albumin. In these "hybrid" animal models, the animals will thus have a range of percentages of human serum albumin and of its own natural albumin in its plasma, e.g., 50% human serum albumin and 50% animal serum albumin, depending on the nature and extent of the introduced human serum albumin genes. These hybrid mice are particularly suited for immunological studies since they will express both types of albumin and may not undergo an immunological reaction to either form of albumin.

However, in another embodiment of the invention, an animal model for drug testing and testing of other materials in environments that will more closely approach human conditions is prepared by introducing a gene for human serum albumin while eliminating the animal's own genes for producing albumin. This type of animal model, resulting in a "knock-out" and "knock-in" mouse, will most closely approach the physiology of the human circulatory system because the animal model in this case will have all of its blood plasma dominated by human serum albumin and will not produce the animal's own natural albumin. As described further below, in the preferred animal model of the invention, it is highly desirable to perform a "knock in" process simultaneously with the procedure wherein the gene coding for the animal's native albumin is knocked out and the gene for human serum albumin is "knocked in" at the same location as the animal's own gene for serum albumin. This is particularly desirable because the inserted gene for human serum albumin will be at the most appropriate location in the genome to interact with the other sequences involved in the operation and expression of the albumin gene, and it is thus more likely that the functioning of the animal and the expression of the albumin will be carried out more normally if the human gene for albumin is inserted at the animal's normal location for the albumin gene.

In accordance with the present invention, any animal that is currently used for lab testing of materials such as drugs, vaccines or other chemical substances, may be used as the animal model for the present invention. In the typical case, the animals used will be non-human mammals, including small mammals such as rabbits, mice, rats, guinea pigs and other rodents. However, larger mammals, such as dogs, are also used in lab testing and can be made transgenic so as to express human serum albumin. In addition, other mammals that have commonly been subject to transgenic processes, such as pigs, sheep, calves and cows, may also be made into transgenic animal models in accordance with the invention if so desired for particular testing.

In this regard, it is contemplated that in addition to being useful as animal models in accordance with the invention, transgenic animals which are constructed in accordance with the invention may be usable in the large scale production of human serum albumin. In this aspect of the invention, it is generally contemplated that those animals which may normally be used for large-scale production of a transgenic products, particularly cows, pigs, sheep or goats, may be utilized which will express human serum albumin in their bloodstream which can then be isolated and purified for use in human applications. In such a case, it would be preferred if the transgenic animal of the invention is one wherein the genetic material coding for the animal's own native albumin is knocked out so that the animal only produces one kind of serum albumin, namely human, which will assist in the isolation and purification of the albumin obtained from transgenic animals expressing human serum albumin in their bloodstream.

As would be recognized by one of ordinary skill in this art, transgenic animals which contain and express human serum albumin can be manufactured in a number of suitable ways which are now well known in the art. For example, the methods of making transgenic mammals such as disclosed in U.S. Pat. Nos. 4,736,866 (Leder et al.) and 4,873,191 (Wagner), both incorporated herein by reference, may be utilized in order to produce the transgenic animal models of the present invention. In addition, numerous other methods of genetically engineering animals so as to insert a particular gene or to express an inserted gene are well known in the art and may be used to produce the transgenic animal models of the present invention.

In the preferred process of the present invention, the nucleic acids coding for human serum albumin may be added to the genome of a host animal by means of P-element derived vectors as disclosed in U.S. Pat. No. 6,291,243, incorporated herein by reference. In this process, the introduction of exogenous genetic material coding for human serum albumin is achieved through the insertion of P element-derived vectors, which include a pair of P element transposase recognized insertion sequences. In the preferred process, the desired albumin gene may be transferred into the host mammal, e.g., through microinjection into mouse oocyte/embryo nuclei to create a germ line transfer of genetic material.

As indicated above, an animal model in accordance with the preferred embodiment of the invention will have the gene coding for human serum albumin inserted into its genome, and this gene will include all necessary regions, including operons, promoters, etc., to ensure that the gene for human serum albumin will be expressed in the animal model. In the particularly preferred embodiment, the transgenic animal model containing and expressing human serum albumin will be an animal which does not express its own serum albumin, and such an animal may be obtained as a natural mutant such as an NAR rat which does not express its own albumin. Alternatively, the animal model may have its own gene for albumin "knocked out" by any of the currently available genetic knock-out techniques well known to those skilled in the art, e.g., those techniques disclosed, for example, in U.S. Pat. Nos. 5,767,337 and 6,194,633, and in Westphal, C. H. and Leder, P. "Transposon-Generated 'Knock-Out' and 'Knock-In' Gene-Targeting Constructs for Use in Mice" Current Biology 7:R530–R533 (1997), all of these references incorporated herein by reference. As indicated above, in cases where the "knock out" of the animal's own gene for albumin is to be performed in conjunction with the transfection of the animal so as to insert the human gene for albumin, this is preferably done by performing the "knock in" operation at the same time so that the human albumin gene will replace the animal's albumin gene at its proper location in the genome. As another possibility, as also indicated above, it is possible to insert a human serum albumin gene into the genome of the animal model without knocking out the animal's own genetic instructions for producing albumin, and this will result in the production of "hybrid" mice that produce human serum albumin in addition to their own native albumin.

In another embodiment of the present invention, an animal model capable of more accurately reflecting the likely reaction in the bloodstream of potential therapeutic compounds is provided which comprises a non-human mammal which is incapable, either via a natural mutation or via a procedure to knock out the serum albumin gene, of producing its own serum albumin. In such animal models, it is intended that human serum albumin may be injected into said albumin-deficient mammal, and the resulting animal retains the injected human serum albumin and thus may be used as an animal model to assess drugs or other therapeutic compounds that may be ingested by or administered to humans. In this embodiment, an appropriate animal is selected which either has been bred not to express serum albumin, or is a natural mutant animal, such as an NAR rat, which does not express its own serum albumin. Still further, it is possible to utilize an animal in which the gene for serum albumin is knocked out via conventional genetic techniques. In any of these cases, the animal is selected which does not contain or express its own albumin, and the animal model in accordance with the invention is constructed by then injecting a suitable amount of human serum albumin in the bloodstream which is retained in the animal's bloodstream for suitable periods to allow the animal to be used as an animal model.

In accordance with the present invention, it is also contemplated that animal models will be constructed which will which reflect the various genetic diseases and disease states and which also incorporate and express a gene for human serum albumin. For example, an animal model in accordance with the invention may also be constructed with any of a variety of genetic diseases, e.g., hemophilia, sickle cell anemia, etc., or may be used to assess pathogenic diseases, and will also express or contain human serum albumin in its bloodstream. These animal models in accordance with the invention will thus be particularly useful in methods of assessing drugs utilized to treat or prevent such genetic diseases or disease conditions caused by other pathogens.

In general, the animal models of the present invention will thus be useful for testing of the efficacy or toxicology of drugs or other chemicals, such as product additives, in any of the numerous conventional methods presently used by those skilled in the art for such testing using animal models. These tests commonly involve the administration of a suitable amount of a drug or other chemical agent to be assessed into an animal model such as a mouse, rat, guinea pig or other appropriate non-human mammal followed by the close examination of the animal model to determine the efficacy or toxicity of the administered or injected agent. The animal models of the present invention as described above may be utilized in place of the models currently used and will thus be more accurate in determining the true efficacy or toxicity of such drugs or other chemical, physical or biological agent in humans because the administered compound or substance will be introduced into an environment which far more closely mimics that which will be faced in humans.

In one particular application of the animal models of the present invention, the models may be used to test the safety and efficacy of albumin mutations or substitutes which may be administered to human or animal patients to improve oxygen transport capability or which may be used when needed, such as during a blood transfusion in locations wherein natural blood is scarce or unavailable. For example, the animal models of the invention may be utilized to test blood substitutes such as the oxygen-transporting albumin as disclosed in U.S. Pat. No. 5,948,609, incorporated herein by reference. In addition, the models of the invention may be useful in testing other modified forms of albumin such as the modified serum albumins disclosed in PCT Publication WO 02/05645, also incorporated herein by reference.

In another embodiment of the present invention, the animal models of the invention will be useful in testing the immunogenicity or other immunological properties of vaccines or other materials using conventional methods in this field which currently use animal models as a means of assessing efficacy or reactions to new vaccines. In particular, the use of the animal models of the present invention will be far more suitable in assessing the immunogenic reaction in an environment such as the human bloodstream because the animal model of the invention will contain and/or express human serum albumin. In one particular application of the invention, the models will be of particular use in cases wherein molecules or compounds are coupled with albumin in fusion proteins wherein the albumin assists in extending the capacity of the compound to stay in the bloodstream without dissolving. Alternatively, fusion proteins wherein a drug or other compound is fused with human albumin are produced in which the albumin provides a particular timed-release of the active ingredient. In any event, the animal models of the present invention which express human serum albumin are suitable models to test such albumin-containing fusion proteins because they are less likely to treat the albumin of the fusion protein as a foreign object. Accordingly, use of the albumin models to assess the immunogenicity or other properties or reactions of these fusion proteins will be far more reflective of how those fusion proteins will react in the human bloodstream. In these applications which are suitable for the models of the present invention, it is again contemplated that the use of the animal models of the invention will be the same as that which is undergone for animal models which do not express human serum albumin, and that the present invention will thus be suitable for use in any conventional immunological or other testing currently used in the field which employs conventional animal models.

In summary, the animal models of the present invention can be utilized for any of the purposes conventional animal models are used presently, and such animals in accordance with the present invention will afford a more accurate picture of the way that drugs or other physical, chemical or biological agents will react in the human body.

It is thus submitted that the foregoing embodiments are only illustrative of the claimed invention and not limiting of the invention in any way, and alternative embodiments that would be obvious to one skilled in the art not specifically set forth above also fall within the scope of the claims.

The following examples are presently only as illustrative of certain aspects of the present invention and do not act to limit the scope of the invention in any way.

EXAMPLES

Example 1

Injection of Albumin into NAR Rats

In accordance with the present invention, a natural mutant rat which does not express or contain its own serum albumin, namely an NAR rat identified as ODNAR10, was utilized as an animal model in accordance with the present invention by injecting the animal with suitable amounts of human serum albumin. In this example, the NAR was given intravenous albumin injection/infusions by initially injecting relatively small amounts of HSA solution into the animal (1 mL). The amount of blood administered to this initial NAR rat was monitored over a 25 day period and this monitoring showed that a significant amount of human albumin had accumulated in the rat's system during this time, as shown by the chromatograph of FIG. 1, wherein column 10 represents the blood sample obtained from ODNAR10. By the end of the treatment (when the animal expired during anesthesia), ODNAR10 had received a total of 2.125 g HSA administered over a 25 day period (Table I).

Following the administration of albumin to ODNAR10, injections of HSA were given to a second NAR rat identified as ODNAR14, this time a female who had proven barren in the breeding program. It was estimated that if the animal's total blood volume was 25 mL and the "normal" concentration of albumin in a mammal is about 40 mg/mL, then she would have about 1 g of albumin in her blood. On the assumption that the albumin in plasma represents approximately half of the total body albumin, this rat would have about 2 g of albumin in her total body compartments. To allow for losses through natural turnover during the time over which albumin would be administered (half-life of albumin=17 d), as well as some degradation by the immune and other systems, we aimed to administer 3 g over about a 10 day period (Table II). Albumin was administered at a rate of 2.5 ml (625 mg) every few days (see Table II) and blood was drawn immediately prior to each injection of albumin for SDS-PAGE analysis.

FIG. 2 shows the results of this experiment. As can be seen, albumin is present in the serum of this rat at the first time-point of blood collection after initiation of albumin injections (FIG. 2, lane 9) and appears to accumulate throughout the duration of the experiment (compare lanes 9 through 6 which represent blood drawn after sequential albumin injections, with lane 9 showing the results after the first bleed, lane 8 showing the results after the second bleed and so on until the $4^{th}$ bleed shown in lane 6). A rough concentration estimate comparing the amount of albumin in the plasma of ODNAR14 at the 4th post HSA injections bleed (FIG. 2, lane 6) with the normal amount in the plasma of a Sprague-Dawley control rat (FIG. 2, lane 2), indicates that our procedure has introduced approximately 25–40% of normal albumin levels into ODNAR14's plasma. Still further albumin may be injected wherein it is desired to increase the level of human albumin further in accordance with the invention, and accordingly it is contemplated that additional procedures, such as a continual infusion of albumin over a longer time or more frequent administration or injections of yet larger volumes, may result in still higher plasma albumin levels. Thus, the animals with injected human serum albumin in accordance with the present invention may suitably be used to test or otherwise assess drugs or other compounds, such as camptothecin compounds, and will thus be useful in replacing conventional animal models currently used in such testing.

TABLE I

Dates and Amounts of HSA Injected into Pioneer NAR rat (ODNAR10) To Investigate the Distribution of HSA into Plasma

| DATE(a) | BLOOD DRAWN | AMOUNT HSA(b) ADMINISTERED(c) |
|---|---|---|
| 27 Feb. 2002 | Pre albumin administration | None |
| 30 Apr. 2002 | No | 1 mL (250 mg) |
| 02 May 2002 | Yes | 1 mL (250 mg) |
| 06 May 2002 | Yes | 1 mL (250 mg) |
| 10 May 2002 | Yes | 1 mL (250 mg) |
| 22 May 2002 | Yes | 2 mL (500 mg) |
| 25 May 2002 | Yes | 2.5 mL (625 mg) |
| 28 May 2002 | Died | in anesthesia |

(a)Total period over which albumin was administered was 25 days.
(b)Plasbumin-25; Bayer Albumin (Human) 25% (250 mg/mL), Lot number 684W027, Manufacturing date = 11 Apr. 2000, Expiry date = 11 Apr. 2003, Code = 684–71.
(c)Total amount of albumin administered prior to death of animal was 2.125 g.

TABLE II

Dates and Amounts of HSA Injected into Second NAR rat (ODNAR14) To Investigate the Distribution of HSA into Plasma

| DATE(a) | BLOOD DRAWN | AMOUNT HSA(b) ADMINISTERED(c) |
|---|---|---|
| 28 May 2002 | Pre albumin administration | 2.5 mL (625 mg) |
| 30 May 2002 | Yes | 2.5 mL (625 mg) |
| 03 Jun. 2002 | Yes | 2.5 mL (625 mg) |
| 05 Jun. 2002 | Yes | 2.5 mL (625 mg) |
| 07 Jun. 2002 | Yes | 2.5 mL (626 mg) |

(a)Total period over which albumin was administered was 10 days.
(b)Plasbumin-25; Bayer Albumin (Human) 25% (250 mg/mL), Lot number 684W027, Manufacturing date = 11 Apr. 2000, Expiry date = 11 Apr. 2003, Code = 684–71.
(c)Total amount of albumin administered to animal was 3.125 g.

Example 2

Transgenic NAR Rats

In accordance with the present invention, transgenic animal models were prepared which were transfected with the gene for human serum albumin. In this example, first generation NAR rat pups were sent to TOSK for injection of the HSA gene within their proprietary STEALTHGENE vector. Pups were sent to TOSK between the weights of 80 and 120 g, as per their instructions, due to their procedure being most amenable to this age and weight of rat. From the breeding program we have instigated for NAR rats, we have learned that females need to be on the order of 230 g before they conceive reliably. As of today, our heaviest females returned from TOSK have been transfected with the gene for human serum albumin and are 185.5 g and 190 g and growing at a rate of about 15 g every 3 to 4 days. In accordance with the invention, these animals are thus suitable as models for animal testing, and because they have been genetically transformed, such animals will be useful in that when bred, they will pass on the gene coding for human serum albumin to their offspring.

In the preferred breeding program in accordance with the invention, the usual procedures for producing and breeding a transgenic animal will be followed. In this procedure, first the founders will be bred to non-injected animals to produce heterozygote animals—the F1 generation. Each of these potential heterozygotes will be bred again to non-injected animals to produce the F2 generation of heterozygotes. Whereas the F1 heterozygotes will all be different from one another, each heterozygote individual from within a single litter of the F2 generation will be identical to its littermates with respect to the position and integration number of the HSA gene into its genome. Heterozygous siblings from the F2 generation will be bred together (brother×sister) to produce truly homozygous animals in the F3 generation. Other breeding strategies could be run in parallel. For example, a compound homozygote could be produced by mating two founders together that potentially produced more albumin in its plasma than may eventuate from the "classical" breeding strategy. PCR analysis can be performed on F1 and F2 individuals to establish the presence of the HSA gene. Southern blot analysis will be used also and especially to confirm homozygosity in the F3 generation. In addition, conventional gel experiments can be performed to confirm the production of human serum albumin in the transgenic animals in accordance with the invention.

What is claimed is:

1. A transgenic mouse whose genome comprises a nucleic acid coding for human serum albumin, which is expressed in the mouse's bloodstream, wherein the gene coding for the native mouse serum albumin is replaced by the nucleic acid coding for human serum albumin such that the mouse does not express native mouse serum albumin.

2. A method of testing the efficacy, carcinogenicity, immunogenicity or toxicity of an agent designed to be administered internally to a human selected from the group consisting of vaccines, drugs and other therapeutic compounds comprising the steps of administering internally said agent into the transgenic mouse according to claim 1 and determining the efficacy, carcinogenicity, immunogenicity or toxicity of said agent in said transgenic mouse.

3. The method according to claim 2 wherein the testing is to evaluate the efficacy of a drug or other therapeutic compound.

4. The method according to claim 2 wherein the testing is to evaluate the carcinogenicity or toxigenicity of a drug or other therapeutic compound.

5. The method according to claim 2 wherein the testing is to evaluate the immunogenicity or other immunological properties of a vaccine.

* * * * *